United States Patent [19]

Saunders et al.

[11] Patent Number: 5,001,148
[45] Date of Patent: Mar. 19, 1991

[54] MEVINIC ACID DERIVATIVES

[75] Inventors: Jeffrey O. Saunders, Holland, Pa.; Eric M. Gordon, Pennington, N.J.

[73] Assignee: E. R. Squibb & Sons, Inc., Princeton, N.J.

[21] Appl. No.: 362,899

[22] Filed: Jun. 7, 1989

[51] Int. Cl.⁵ ............ A61K 31/365; A61K 31/215; C07D 309/10; C07C 69/78

[52] U.S. Cl. ............................ 514/459; 560/1; 560/11; 560/12; 560/13; 560/17; 560/20; 560/22; 560/23; 560/27; 560/29; 560/31; 560/32; 560/47; 560/49; 560/64; 560/65; 560/73; 560/105; 560/107; 560/121; 560/123; 560/125; 560/127; 560/148; 560/159; 560/160; 560/161; 560/162; 560/124; 514/333; 514/336; 514/341; 514/342; 514/343; 514/354; 514/355; 514/356; 514/438; 514/448; 514/444; 514/269; 514/274; 514/256; 514/369; 514/365; 514/258; 514/300; 514/301; 514/302; 514/247; 514/406; 514/407; 514/225; 514/460; 514/510; 514/824; 514/227.5; 514/227.8; 514/231.8; 514/232.2; 514/237.2; 514/235.8; 514/237.5; 514/316; 514/318; 514/326; 514/330; 514/331; 514/422; 514/426; 514/423; 514/397; 514/398; 514/400; 514/332; 558/416; 549/292; 549/59; 549/60; 549/64; 549/65; 546/113; 546/114; 546/115; 546/117; 546/255; 546/256; 546/263; 546/281; 546/280; 546/275; 546/278; 546/187; 546/189; 546/191; 546/194; 546/206; 544/58.4; 544/58.5; 544/58.6; 544/58.7; 544/149; 544/129; 544/159; 544/160; 544/163; 544/162; 544/333; 544/334; 544/335; 544/336; 544/338; 544/279; 544/286; 544/251; 544/253; 548/251; 548/253; 548/336; 548/337; 548/374; 548/376; 548/377; 548/378

[58] Field of Search ............ 549/292, 60, 64, 65, 549/59; 514/824, 459, 460, 227.5, 227.8, 231.8, 510, 232.2, 237.2, 235.8, 237.5, 316, 318, 326, 336, 331, 422, 426, 423, 397, 398, 460, 332, 333, 336, 341, 342, 343, 354, 355, 356, 438, 448, 449, 269, 274, 256, 369, 365, 258, 300, 301, 362, 247, 406, 407, 225; 560/1, 11, 12, 13, 17, 20, 256, 22, 23, 121, 27, 29, 31, 123, 124, 107, 32, 47, 49, 64, 65, 73, 105, 125, 127, 148, 159, 160, 161, 162; 558/416; 548/318, 326, 518, 523, 50, 535, 536, 251, 253, 336, 337, 374, 376, 377, 391; 544/58.4, 58.5, 58.6, 58.7, 149, 129, 159, 160, 162, 163, 333, 334, 335, 336, 338, 279, 286, 251, 253; 546/113, 114, 115, 117, 255, 256, 263, 281, 280, 275, 271, 187, 189, 191, 194, 206

[56] References Cited

U.S. PATENT DOCUMENTS

| | | | |
|---|---|---|---|
| 3,983,140 | 9/1976 | Endo et al. | 260/343.5 |
| 4,049,495 | 9/1977 | Endo et al. | 195/36 |
| 4,231,938 | 11/1980 | Monaghan et al. | 260/343.5 |
| 4,346,227 | 8/1982 | Terahara et al. | 560/119 |
| 4,410,629 | 10/1983 | Terahara et al. | 435/146 |
| 4,444,784 | 4/1984 | Hoffman et al. | 424/279 |
| 4,448,979 | 5/1984 | Terahara et al. | 549/292 |
| 4,450,171 | 5/1984 | Hoffman et al. | 424/279 |
| 4,857,546 | 8/1989 | Duggan et al. | 514/460 |

FOREIGN PATENT DOCUMENTS

| | | |
|---|---|---|
| 0065835 | 5/1982 | European Pat. Off. |
| 0251625 | 6/1987 | European Pat. Off. |
| 2075013 | 11/1981 | United Kingdom .......... 560/119 |

OTHER PUBLICATIONS

F. M. Singer et al., "New Inhibitors of in vitro Conversion of Acetate and Mevalonate to Cholesterol", Proc. Soc. Exper. Biol. Med., 102, 370 (1959).

F. H. Hulcher, "Inhibition of Hepatic Cholesterol Biosynthesis by 3,5-Dihydroxy-3,4,4-Trimethylvaleric Acid and its Site of Action", Arch. Biochem. Biophys., 146, 422 (1971).

A. G. Brown et al., "Crystal and Molecular Structure of Compactin, a New Antifungal Metabolite from *Penicillium Brevicompactum*", J. Chem. Soc. Perkin I., 1165–1170 (1976).

Primary Examiner—Richard L. Raymond
Assistant Examiner—M. L. Russell
Attorney, Agent, or Firm—Donald J. Barrack; Timothy J. Gaul

[57] ABSTRACT

Antihypercholesterolemic activity, due to competitive inhibition of HMG CoA reductase, has been found in compounds of the formula

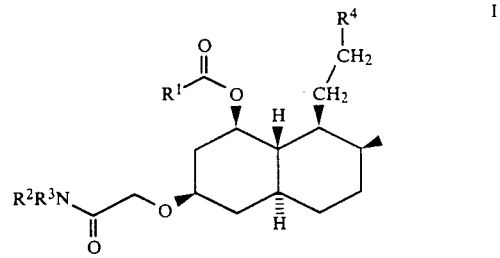

wherein:
$R^1$, $R^2$ and $R^3$ are independently selected from:
(1) alkyl,
(2) substituted alkyl in which one or more substituents are selected from
  (a) halogen,
  (b) hydroxyl,
  (c) alkoxy,
  (d) alkoxycarbonyl,
  (e) acyloxy,
  (f) cycloalkyl,
  (g) phenyl,
  (h) substituted phenyl in which one or more substituents are X or Y,
  (i) alkyl-S(O)$_n$,
  (j) cycloalkyl-S(O)$_n$,
  (k) phenyl-S(O)$_n$,
  (l) substituted phenyl-S(O)$_n$ in which one or more substituents are X or Y, and
  (m) oxo, (Abstract continued on next page.)

(3) alkoxy,
(4) alkenyl,
(5) cycloalkyl,
(6) substituted cycloalkyl in which one or more substituents are selected from
  (a) alkyl,
  (b) substituted alkyl in which one or more substituents are selected from
    (i) halogen,
    (ii) hydroxy,
    (iii) alkoxy,
    (iv) alkoxycarbonyl
    (v) acyloxy
    (vi) phenyl
    (vii) substituted phenyl in which one or more substituents are X and Y,
    (viii) alkyl-S(O)$_n$,
    (ix) cycloalkyl-S(O)$_n$,
    (x) phenyl-S(O)$_n$,
    (xi) substituted phenyl-S(O)$_n$ in which one or more substituents are X and Y, and
    (xii) oxo,
  (c) alkyl-S(O)$_n$,
  (d) cycloalkyl-S(O)$_n$,
  (e) phenyl-S(O)$_n$,
  (f) substituted phenyl-S(O)$_n$ in which one or more substituents are X or Y,
  (g) halogen,
  (h) hydroxy,
  (i) alkoxy,
  (j) alkoxycarbonyl,
  (k) acyloxy,
  (l) phenyl, and
  (m) substituted phenyl in which one or more substituents are X and Y,
(7) phenyl,
(8) substituted phenyl in which one or more substituents are X or Y,
(9) amino,
(10) alkylamino,
(11) dialkylamino,
(12) phenylamino,
(13) substituted phenylamino in which one or more substituents are X or Y,
(14) alkyl(substituted phenyl)amino in which one or more substituents are X and Y,
(15) phenylalkylamino,
(16) di(phenylalkyl)amino,
(17) substituted phenylalkylamino in which one or more substituents are X or Y,
(18) a member selected from
  (a) piperidinyl,
  (b) pyrrolidinyl,
  (c) piperazinyl,
  (d) morpholinyl,
  (e) thiomorpholino,
  (f) histaminyl,
  (g) 3-aminomethyl pyridinyl, and
(19) hydroxy substituted alkylamino;

X and Y are independently hydrogen, halogen, trifluoromethyl, alkyl, nitro, alkoxy, or cyano;

n is 0, 1, or 2;

$R^4$ is

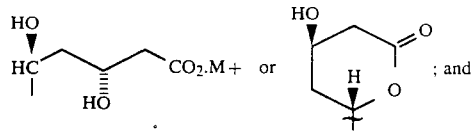

M+ is hydrogen, ammonium, or an alkali metal.

13 Claims, No Drawings

MEVINIC ACID DERIVATIVES

FIELD OF THE INVENTION

The present invention relates to mevinic acid derivatives that inhibit 3-hydroxy-3-methylglutaryl coenzyme A (HMG CoA) reductase, an enzyme used in cholesterol biosynthesis. The compounds of this invention are, therefore, useful as antihypercholesterolemic agents.

BACKGROUND OF THE INVENTION

F. M. Singer et al., "New Inhibitors of in vitro Conversion of Acetate and Mevalonate to Cholesterol", Proc. Soc. Exper. Biol. Med., 102, 370 (1959) and F. H. Hulcher, "Inhibition of Hepatic Cholesterol Biosynthesis by 3,5-Dihydroxy-3,4,4,-trimethylvaleric Acid and its Site of Action," Arch. Biochem. Biophys., 146, 422 (1971) disclose that certain mevalonate derivatives inhibit the biosynthesis of cholesterol.

Singer et al. reported that fluoromevalonic acid is more effective in inhibiting biosynthesis of cholesterol (as measured by in vitro conversion of labeled acetate and labeled mevalonate into cholesterol) than Δ4-androstene-17α-ol-3-one-17β-oic acid and Δ1-testololactone.

Hulcher reported that an analog of mevalonic acid (3,5-dihydroxy-3,4,4-trimethylvaleric acid) strongly inhibits cholesterol biosynthesis by rat liver homogenates.

U.S. Pat. No. 3,983,140 to Endo et al. discloses the fermentation product ML-236B, referred to generically as compactin and mevastatin, which has the structure

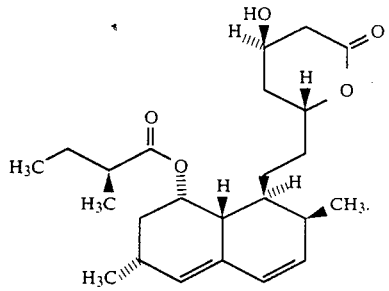

A

This compound is prepared by cultivation of a microorganism of the genus Penicillium. The fermentation process is disclosed in U.S. Pat. No. 4,049,495 issued Sept. 20, 1977 to Endo et al.

Brown, A. G., et al., (Beecham Pharmaceuticals Research Div.), "Crystal and Molecular Structure of Compactin, a New Antifungal Metabolite from Penicillium Brevicompactum", J. Chem. Soc. Perkin I. 1165-1170 (1976) confirms that compactin has the complex mevalonolactone structure disclosed by Endo et al. in the above patents.

U.S. Pat. No. 4,231,938 to Monaghan et al. discloses mevinolin (also called lovastatin, Monacolin K, and MK-803), which has the structure

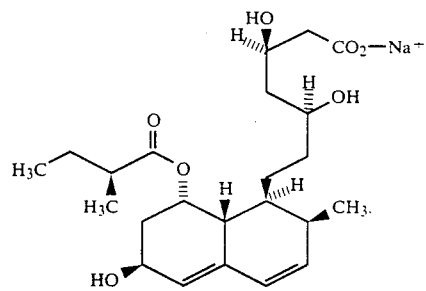

B

This compound is prepared by culturing a microorganism of the genus Aspergillus.

U.S. Pat. No. 4,346,227 to Terahara et al. discloses pravastatin, which has the structure

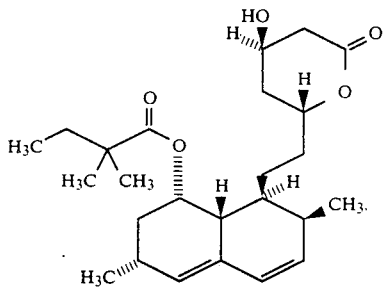

C

Pravastatin is prepared by the enzymatic hydroxylation of compactin or its carboxylic acid, as disclosed in U.S. Pat. No. 4,410,629 to Terahara et al.

U.S. Pat. No. 4,448,979, issued May 15, 1984 to Terahara et al., discloses the lactone of pravastatin.

U.S. Pat. Nos. 4,444,784 and 4,450,171 to Hoffman et al disclose various antihypercholesterolemic compounds, including synvinolin (simvastatin), which has the structure

D

The Hoffman patents further disclose compounds of the structures

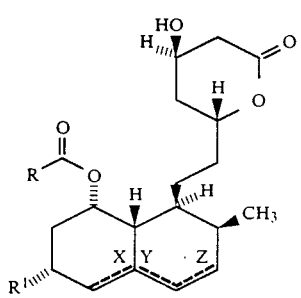

E

-continued
and

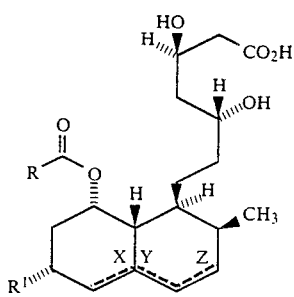
F wherein $R^1$ is H or $CH_3$, R can be an alkyl group including

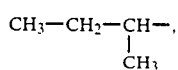

X, Y and Z are single and/or double bonds in all possible combinations.

European Patent Application No. 0065835A1, filed by Sankyo, discloses cholesterol biosynthesis-inhibiting compounds of the structure

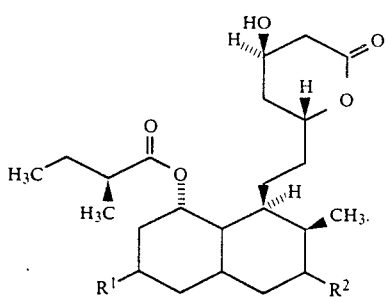
G

The same application discloses the corresponding free carboxylic acids, which may be represented by the formula

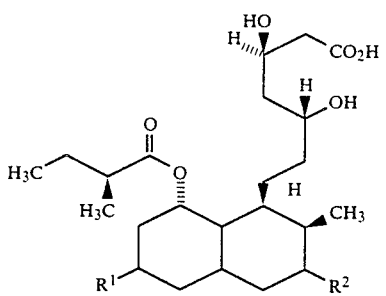
H in which one of $R^1$ and $R^2$ represents a hydrogen atom and the other represents a hydroxy group. The Sankyo application further discloses salts and esters of the carboxylic acids.

European patent application No. 251,625A2 describes a series of polyhydro-mevinolin derivatives in which a methyl group has been oxidized and further derivatized to yield compounds following the formulas

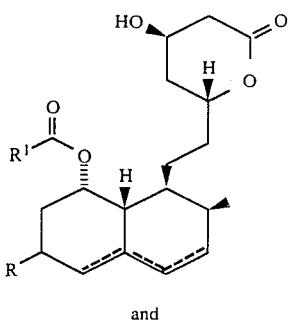
J and

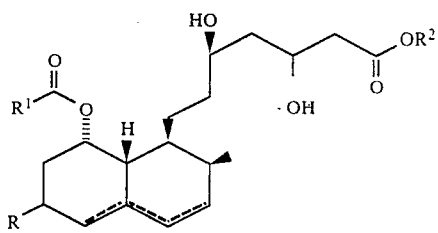
K wherein
R is $CH_2OH$, $CH_2OC(O)R^3$, $CO_2R^4$ or $C(O)NR^6R^7$;
$R^1$ and $R^3$ are independently selected from:
(1) $C_{1-10}$ alkyl;
(2) substituted $C_{1-10}$ alkyl in which one or more substituent(s) is selected from
(a) halogen,
(b) hydroxy,
(c) $C_{1-10}$ alkoxy,
(d) $C_{1-5}$ alkoxycarbonyl,
(e) $C_{1-5}$ acyloxy,
(f) $C_{3-8}$ cycloalkyl,
(g) phenyl,
(h) substituted phenyl in which the substituents are X and Y,
(i) $C_{1-10}$ alkyl $S(O)_n$ in which n is 0 to 2,
(j) $C_{3-8}$ cycloalkyl $S(O)_n$,
(k) phenyl $S(O)_n$,
(l) substituted phenyl $S(O)_n$ in which the substituents are X and Y, and
(m) oxo;
(3) $C_{1-10}$ alkoxy;
(4) $C_{2-10}$ alkenyl;
(5) $C_{3-8}$ cycloalkyl;
(6) substituted $C_{3-8}$ cycloalkyl in which on substituent is selected from
(a) $C_{1-10}$ alkyl,
(b) substituted $C_{1-10}$ alkyl in which the substituent is selected from
(i) halogen,
(ii) hydroxy,
(iii) $C_{1-10}$ alkoxy,
(iv) $C_{1-5}$ alkoxycarbonyl,
(v) $C_{1-5}$ acyloxy,
(vi) phenyl,
(vii) substituted-phenyl in which the substituents are X and Y,
(viii) $C_{1-10}$ alkyl $S(O)_n$,
(ix) $C_{3-8}$ cycloalkyl $S(O)_n$,
(x) phenyl $S(O)_n$,
(xi) substituted phenyl $S(O)_n$ in which the substituents are X and Y and
(xii) oxo,
(c) $C_{1-10}$ alkyl $S(O)_n$, (d) $C_{3-8}$ cycloalkyl $S(O)_n$,
(e) phenyl $S(O)_n$,
(f) substituted phenyl $S(O)_n$ in which the substituents are X and Y,
(g) halogen,
(h) hydroxy,
(i) $C_{1-10}$ alkoxy,
(j) $C_{1-5}$ alkoxycarbonyl,
(k) $C_{1-5}$ acyloxy,
(l) phenyl, and
(m) substituted phenyl in which the substituents are X and Y;
(7) phenyl;
(8) substituted phenyl in which the substituents are X and Y;
(9) amino;
(10) $C_{1-5}$ alkylamino;
(11) di($C_{1-5}$alkyl)amino;
(12) phenylamino;
(13) substituted phenylamino in which the substituents are X and Y;
(14) phenyl $C_{1-10}$ alkylamino;
(15) substituted phenyl $C_{1-10}$ alkylamino in which the substituents are X and Y;
(16) a member selected from
  (a) piperidinyl,
  (b) pyrrolidinyl,
  (c) piperazinyl,
  (d) morpholinyl, and
  (e) thiomorpholinyl; and
(17) $R^5S$ in which $R^5$ is selected from
  (a) $C_{1-10}$ alkyl,
  (b) phenyl, and
  (c) substituted phenyl in which the substituents are X and Y;
$R^2$ and $R^4$ are independently selected from:
(1) hydrogen;
(2) $C_{1-5}$ alkyl;
(3) Substituted $C_{1-5}$ alkyl in which the substituent is selected from
  (a) phenyl,
  (b) dimethylamino, and
  (c) acetylamino; and
(4) 2,3-dihydroxypropyl;
$R^6$ and $R^7$ are independently selected from
(1) hydrogen;
(3) substituted $C_{1-10}$ alkyl in which one or more substituent(s) is selected from
  (a) halogen,
  (b) hydroxy
  (c) $C_{1-10}$ alkoxy,
  (d) $C_{1-10}$ alkoxycarbonyl,
  (e) $C_{1-5}$ acyloxy,
  (f) $C_{3-8}$ cycloalkyl,
  (g) phenyl,
  (h) substituted phenyl in which the substituents are X and Y,
  (i) $C_{1-10}$ alkyl $S(O)_n$ in which n is 0 to 2.
  (j) $C_{3-8}$ cycloalkyl $S(O)_n$,
  (k) phenyl $S(O)_n$,
  (l) substituted phenyl $S(O)_n$ in which the substituents are X and Y, and
  (m) oxo;
(4) $C_{2-10}$ alkenyl;
(5) $C_{3-8}$ cycloalkyl;
(6) aminocarbonyl;
(7) substituted aminocarbonyl in which one or more substituent(s) is selected from
  (a) $C_{1-5}$ alkyl,
  (b) $C_{3-8}$ cycloalkyl,
  (c) phenyl, and
  (d) substituted phenyl in which the substituents are X and Y;
(8) phenyl;
(9) substituted phenyl in which the substituents are X and Y;
(10) $C_{1-10}$ alkylcarbonyl;
(12) phenylcarbonyl;
(13) substituted phenylcarbonyl in which the substituents are X and Y; and
(14) a nitrogen-containing heterocyclic group such as piperidinyl, pyrrolidinyl, piperazinyl, morpholinyl or the like formed by joining the substituents $R^6$ and $R^7$ to form a heterocyclic ring; and X and Y independently are hydrogen, halogen, trifluoromethyl $C_{1-3}$ alkyl, nitro, cyano or group selected from:
(1) $R^8O(CH_2)_m$ in which m is 0 to 3 and $R^8$ is hydrogen, $C_{1-3}$ alkyl or hydroxy-$C_{2-3}$ alkyl;
(2)

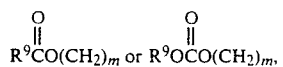

in which $R^9$ is hydrogen, $C_{1-3}$ alkyl, hydroxy-$C_{2-3}$ alkyl, phenyl, naphthyl, amino-$C_{1-3}$ alkyl, $C_{1-3}$ alkylamino-$C_{1-3}$ alkyl, di($C_{1-3}$ alkyl)amino-$C_{1-3}$ alkyl, hydroxy-$C_{2-3}$ alkylamino-$C_{1-3}$ alkyl or di(hydroxy-$C_{2-3}$ alkyl)amino-$C_{1-3}$ alkyl;
(3)

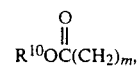

in which $R^{10}$ is hydrogen, $C_{1-3}$ alkyl, hydroxy-$C_{2-3}$ alkyl, $C_{1-3}$ alkoxy-$C_{1-3}$ alkyl, phenyl or naphthyl;
(4) $R^{11}R^{12}N(CH_2)_m$,

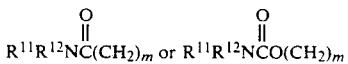

in which $R^{11}$ and $R^{12}$ independently are hydogen, $C_{13}$ alkyl, hydroxy-$C_{2-3}$ alkyl or together with the nitrogen atom to which they are attached form a heterocyclic group selected from piperidinyl, pyrrolidinyl, piperazinyl, morpholinyl or thiomorpholinyl;
(5) $R^{13}S(O_n(CH_2)_m$ in which $R^{13}$ is hydrogen, $C_{1-3}$ alkyl, amino, $C_{1-3}$ alkylamino or di($C_{1-3}$ alkyl)amino;
and wherein a, b and c each represent single bonds or one of a, b and c represents a double bond or both a and c represent double bonds; or a pharmaceutically acceptable salt thereof.

SUMMARY OF THE INVENTION

Antihypercholesterolemic activity has now been discovered in compounds having the formula

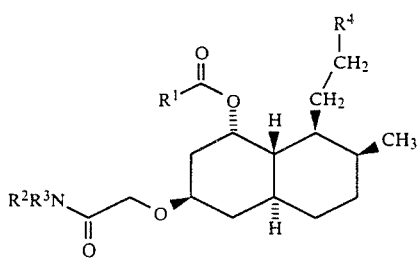

wherein, in formula I and throughout this specification, $R^1$, $R^2$ and $R^3$ are independently selected from:
(1) alkyl,
(2) substituted alkyl in which one or more substituents are selected from
 (a) halogen,
 (b) hydroxyl,
 (c) alkoxy,
 (d) alkoxycarbonyl,
 (e) acyloxy,
 (f) cycloalkyl,
 (g) phenyl,
 (h) substituted phenyl in which one or more substituents are X or Y,
 (i) alkyl-S(O)$_n$,
 (j) cycloalkyl-S(O)$_n$,
 (k) phenyl-S(O)$_n$,
 (l) substituted phenyl-S(O)$_n$ in which one or more substituents are X or Y, and
 (m) oxo,
(3) alkoxy,
(4) alkenyl,
(5) cycloalkyl,
(6) substituted cycloalkyl in which one or more substituents are selected from
 (a) alkyl,
 (b) substituted alkyl in which one or more substituents are selected from
  (i) halogen,
  (ii) hydroxy,
  (iii) alkoxy,
  (iv) alkoxycarbonyl
  (v) acyloxy
  (vi) phenyl
  (vii) substituted phenyl in which one or more substituents are X or Y,
  (viii) alkyl-S(O)$_n$,
  (ix) cycloalkyl-S(O)$_n$,
  (x) phenyl-S(O)$_n$,
  (xi) substituted phenyl-S(O) in which one or more substituents are X or Y, and
  (xii) oxo,
 (c) alkyl-S(O)$_n$,
 (d) cycloalkyl-S(O)$_n$,
 (e) phenyl-S(O)$_n$,
 (f) substituted phenyl-S(O)$_n$ in which one or more substituents are X or Y,
 (g) halogen,
 (h) hydroxy,
 (i) alkoxy,
 (j) alkoxycarbonyl,
 (k) acyloxy,
 (l) phenyl, and
 (m) substituted phenyl in which one or more substituents are X or Y,
(7) phenyl,
(8) substituted phenyl in which one or more substituents are X or Y,
(9) amino,
(10) alkylamino,
(11) dialkylamino,
(12) phenylamino,
(13) substituted phenylamino in which one or more substituents are X or Y,
(14) alkyl(substituted phenyl)amino in which one or more substituents are X or Y,
(15) phenylalkylamino,
(16) di(phenylalkyl)amino,
(17) substituted phenylalkylamino in which one or more substituents are X or Y,
(18) a member selected from
 (a) piperidinyl,
 (b) pyrrolidinyl,
 (c) piperazinyl,
 (d) morpholinyl,
 (e) thiomorpholino,
 (f) histaminyl,
 (g) 3-aminomethyl pyridinyl, and
(19) hydroxy substituted alkylamine;

X and Y are independently hydrogen, halogen, trifluoromethyl, alkyl, nitro, alkoxy, or cyano;

n is 0, 1, or 2;

$R^4$ is

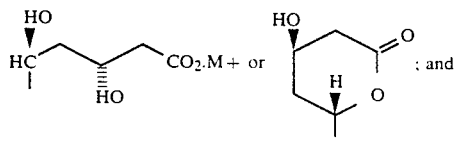

M+ is hydrogen, ammonium, or an alkali metal, such as lithium, sodium, potassium.

Formula I compounds inhibit cholesterol biosynthesis by competitive inhibition of HMG CoA reductase, which is a key enzyme in cholesterol biosynthesis.

DETAILED DESCRIPTION OF THE INVENTION

1. Definition of Terms

Listed below are definitions of various terms used to describe this invention. These definitions apply to the terms as they are used throughout the specification (unless otherwise limited in specific instances) either individually or as part of a larger group. Where exemplary and preferred groups are listed in any definition of a term, these groups are used to illustrate rather than limit the meaning of the term.

The term "alkali metal" refers to lithium, sodium, and potassium.

The term "lower alkyl" or "alkyl" as employed herein by itself or as part of another group includes both straight and branched chain hydrocarbon groups, preferably of 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including one or two halo-substituents, such as F, Br, Cl or I or CF$_3$, an alkoxy substituent, an aryl substituent, an alkyl-aryl substituent, a haloaryl substituent, a cycloalkyl substituent or an alkylcycloalkyl substituent.

The terms "cycloalkyl" and "cycloalkenyl" by themselves or as part of another group include saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups and/or 1 or 2 lower alkoxy groups.

The term "alkenyl" by itself or as part of another group refers to both straight and branched chain groups. Those groups having 2 to 10 carbon atoms are preferred. The term "alkenyl" further includes groups having one or two halo substituents, an alkoxy substituent, an aryl substituent, an alkyl-aryl substituent, a haloaryl substituent, a cycloalkyl substituent, or an alkylcycloalkyl substituent.

The term "halogen" or "halo" refers to fluorine, chlorine, bromine and iodine, as well as $CF_3$.

The term "aryl" or "Ar" as employed herein by itself or as part of another group refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 lower alkyl groups, 1 or 2 halogens (Cl, Br or F), and/or 1 or 2 lower alkoxy groups.

The term "aralkyl", "aryl-alkyl", "alkyl-aryl" or "aryl-lower alkyl" as used herein by itself or as part of another group refers to lower alkyl groups as discussed above having an aryl substituent, such as phenyl.

The term "lower alkoxy" refers to a lower alkyl group linked to an oxygen atom.

The term "acyl" includes all organic moieties that may be derived from an organic acid (i.e., a carboxylic acid) by exchange of the hydroxyl group.

Exemplary acyl groups are:

(a) Aliphatic groups having the formula

wherein $R^5$ is alkyl, cycloalkyl, alkoxy, alkenyl, cycloalkenyl, cyclohexadienyl, or alkyl or alkenyl substituted with one or more halogen, cyano, nitro, amino, mercapto, alkylthio, or cyanomethylthio groups.

(b) Carbocyclic aromatic groups having the formula

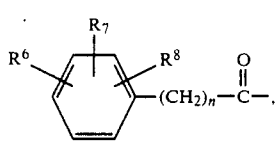

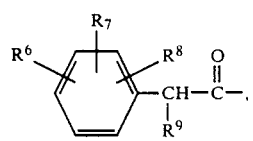

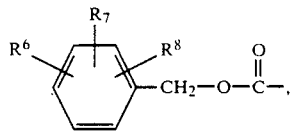

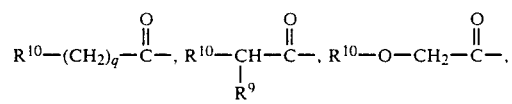

wherein n is 0, 1, 2 or 3; $R^6$, $R^7$, and $R^8$ are independently hydrogen, halogen, hydroxyl, nitro, amino, cyano, trifluoromethyl, alkyl of 1 to 4 carbon atoms, alkyloxy of 1 to 4 carbon atoms or aminomethyl; and $R^9$ is amino, hydroxyl, a carboxyl salt, protected carboxyl, formyloxy, a sulfo salt, a sulfoamino salt, azido, halogen, hydrazino, alkylhydrazino, phenylhydrazino, or [(alkylthio)thioxomethyl]thio.

(c) Heteroaromatic groups having the formula

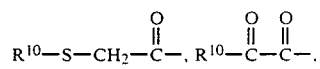

wherein q is 0, 1, 2 or 3; $R^9$ is as defined above; and $R^{10}$ is a substituted or unsubstituted 5-, 6- or 7-membered heterocyclic ring containing 1, 2, 3 or 4 (preferably 1 or 2) nitrogen, oxygen and sulfur atoms. Exemplary heterocyclic rings are thienyl, furyl, pyrrolyl, pyridinyl, pyrazolyl, pyrazinyl, thiazolyl, pyrimidinyl and tetrazolyl. Exemplary substituents are halogen, hydroxyl, nitro, amino, cyano, trifluoromethyl, alkyl of 1 to 4 carbon atoms, alkoxy of 1 to 4 carbon atoms, or

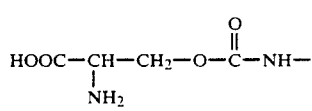

(d) [[(4-Substituted-2,3-dioxo-1-piperazinyl)carbonyl]amino]arylacetyl groups having the formula

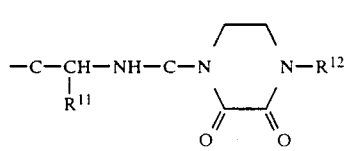

wherein $R^{11}$ is an aromatic group (including carbocyclic aromatics such as those of the formula

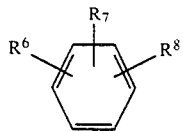

and heteroaromatics as included within the definition of $R^{10}$); and $R^{12}$ is alkyl, substituted alkyl (wherein the alkyl group is substituted with one or more halogen, cyano, nitro, amino or mercapto groups), arylmethyleneamino (i.e., —N=CH—$R^{11}$ wherein $R^{11}$ is as defined above), arylcarbonylamino (i.e.,

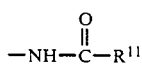

wherein $R^{11}$ is as defined above) or alkylcarbonylamino.

(e) (Substituted oxyimino)arylacetyl groups having the formula

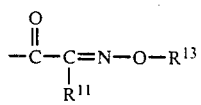

wherein $R^{11}$ is as defined above and $R_{13}$ is hydrogen, alkyl, cycloalkyl, alkylaminocarbonyl, arylaminocarbonyl (i.e.,

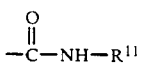

wherein $R^{11}$ is as defined above) or substituted alkyl (wherein the alkyl group is substituted with 1 or more halogen, cyano, nitro, amino, mercapto, alkylthio, aromatic group (as defined by $R^{11}$), carboxyl (including salts thereof), amido, alkoxycarbonyl, phenylmethoxycarbonyl, diphenylmethoxycarbonyl, hydroxyalkoxyphosphinyl, dihydroxyphosphinyl, hydroxy (phenylmethoxy)phosphinyl, or dialkoxyphosphinyl substituents).

(f) (Acylamino)arylacetyl groups having the formula

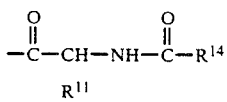

wherein $R^{11}$ is as defined above and $R^{14}$ is

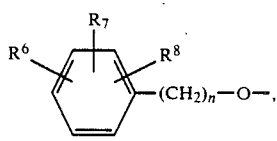

amino, alkylamino, (cyanoalkyl)amino, amido, alkylamido, (cyanoalkyl)amido,

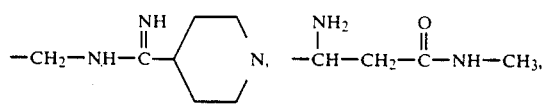

-continued

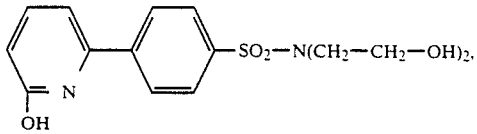

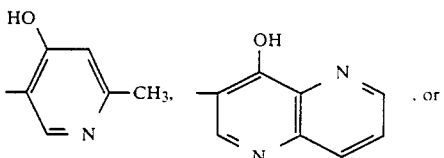

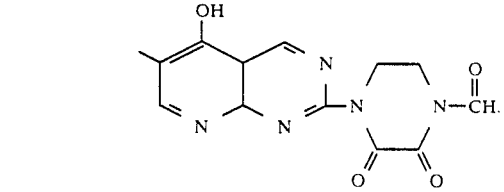

(g) [[[3-Substituted-2-oxo-1-imidazolidinyl]-carbonyl-]amino]arylacetyl groups having the formula

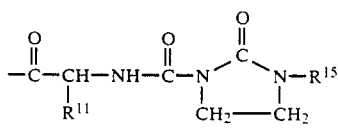

wherein $R^{11}$ is as defined above and $R^{15}$ is hydrogen, alkylsulfonyl, arylmethyleneamino (i.e., —N=CH-$R^{11}$ wherein $R^{11}$ is as defined above),

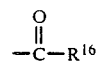

(wherein $R^{16}$ is hydrogen, alkyl or halogen substituted alkyl), aromatic group (as defined by $R^{11}$ above), alkyl or substituted alkyl (wherein the alkyl group is substituted with one or more halogen, cyano, nitro, amino or mercapto groups).

The term "alkoxycarbonyl" refers to alkoxy groups linked to —C=O. Groups having up to 10 carbon atoms are preferred.

The term "acyloxy" refers to acyl groups linked to another oxygen atom. Groups having up to five carbon atoms are preferred.

The term "cycloalkyl" refers to cyclic alkyl groups. Groups having 3 to 8 carbon atoms are preferred.

The term "alkylamine" refers to alkyl groups linked to —$NH_2$. Groups having up to five carbon atoms are preferred.

2. Process of Formation

The compound of this invention may be prepared by the following exemplary and novel process.

Preparation of the compound of the formula

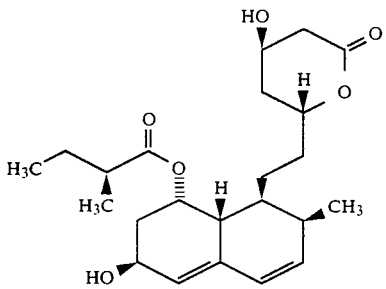

is described in U.S. Pat. Nos. 3,983,140 and 4,346,227. In the process of forming compound I, compound IV may be in sequence:

(1) placed in an inert solvent (e.g., tetrahydrofuran or dichloromethane) under an inert atmosphere (e.g., argon or nitrogen) at a temperature of about 15° to 25° C. and treated with an appropriate silyl protecting agent (e.g., t-butyldimethylsilyl chloride, triethylsilyl chloride, phenyldimethylsilyl chloride or t-butyldiphenylsilyl chloride) in the presence of an appropriate amine base (e.g., imidazole, dimethylaminopyridine, or diisopropylethyl amine);

(2) placed in a degassed suspension of an appropriate metal catalyst (e.g., platinum on carbon) in an inert organic solvent (e.g., ethyl acetate or tetrahydrofuran) and subjected to hydrogen gas under a pressure of 30 to 60 psi; and (3) treated with a different hydroxyl-protecting agent (e.g., benzyloxymethyl bromide (BOM-Br)) under an inert atmosphere in an inert organic solvent (e.g., dichloromethane) and in the presence of an appropriate amine base (e.g., N,N-dimethylaniline) at a temperature of about 15° to 30° C., preferably 20° to 25° C.

Compound IV may thus be selectively protected initially at the hexahydronaphthanelic hydroxyl group, hydrogenated selectively to trans-fused decalin, and protected at the lactone hydroxyl group to yield a compound of the formula III

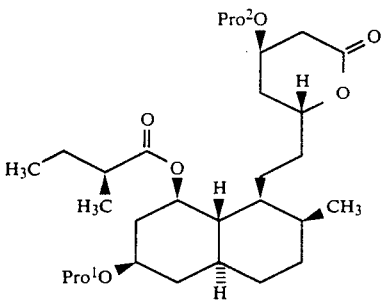

wherein $Pro^1$ is a silyl hydroxyl-protecting group such as

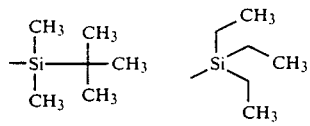

and the like, and wherein $Pro^2$ is a hydroxyl-protecting group such as

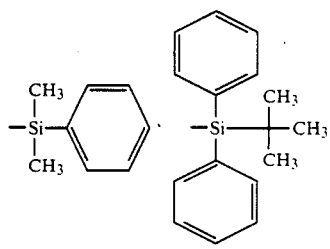

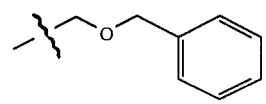

and the like.

Compound III may be, in sequence:

(1) placed in an appropriate organic solvent (e.g., acetonitrile), cooled to about $-30°$ to $-10°$ C. (preferably $-20°$ C.) and treated with a suitable fluoride desilating agent (e.g., HF-pyridine, HF (aqueous), or tetrabutylammonium fluoride) for about 0.5 to 2 hours, with warming to about $-5°$ to $5°$ C. after about 1 to 1.5 hours;

(2) placed in an appropriate organic solvent (e.g., dichloromethane) under an inert atmosphere (e.g., argon) at about 15° to 25° C. and stirred with a suitable catalyst (e.g., $[Rh(OAc)_2]_2$) for about 15 to 60 minutes, followed by treatment with an alkyl diazoacetate (preferably ethyl diazoacetate) over a period of about 2 to 6 hours;

(3) placed in an inert organic solvent (e.g., ethyl acetate or tetrahydrofuran) in the presence of an appropriate catalyst (e.g., palladium hydroxide on carbon) and treated with a hydrogen source (e.g., hydrogen gas);

(4) placed in an appropriate organic solvent (e.g., acetonitrile, tetrahydrofuran or dioxane) at about $-5°$ to $5°$ C. and treated with a solution of aqueous hydroxide (e.g., lithium, sodium or potassium hydroxide) for 5 to 15 minutes, with warming to 15° to 25° C. for an additional 30 to 90 minutes; and (5) placed in a suitable organic solvent (e.g., ethyl acetate) and about $-5°$ to $5°$ C. and treated with an appropriate non-mineral acid (e.g., trifluoroacetic acid, Amberlyst ® 15).

As a result, compound III may undergo selective mono-deprotection, etherification, hydrogenolysis, bissaponification and relactonization, respectively, to form a compound of the formula

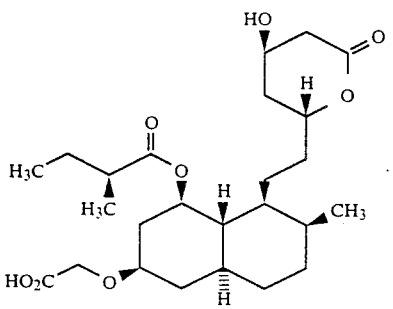

Compound II may be placed in an appropriate organic solvent (e.g., tetrahydrofuran) for about −5° to 5° C. and subjected to amidation under appropriate carboxylic acid activiating conditions, preferably through sequential treatment with:

(1) 1-hydroxybenzotriazole hydrate;
(2) a suitable primary or secondary amine; and
(3) 1,3-dicyclohexylcarbodiimide; so that compound II may undergo amidation to form a compound having the formula

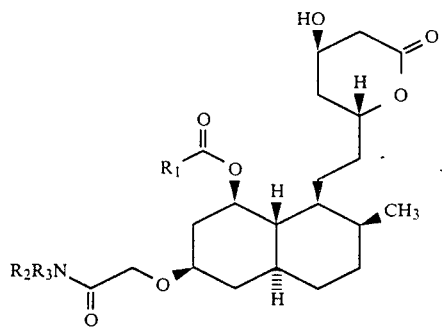

Compound IA may be placed in an organic solvent (e.g., dioxane) at about −5° to 5° C., treated with an appropriate hydroxide (preferably lithium hydroxide), and warmed to about 15° to 25° C. after 5 to 20 minutes for an additional 30 to 60 minutes to form a compound of the formula

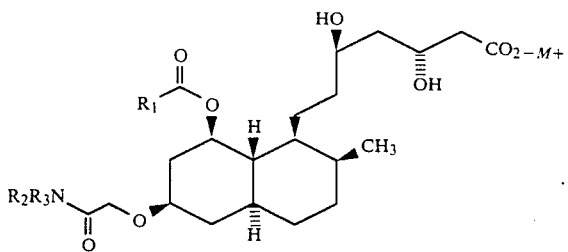

Compounds IA and IB within the scope of formula I.

3. Use and Utility

The compound of formula I of the invention will be formulated with a pharmaceutical vehicle or diluent. The pharmaceutical composition can be formulated in a classical manner utilizing solid or liquid vehicles or diluents and pharmaceutical additives of a type appropriate to the desired mode of administration. The compounds can be administered by an oral route in the form of tablets, capsules, granules or powders, for example, or by a parenteral route in the form of injectable preparations.

A typical capsule for oral administration contains active ingredients (25 mg), lactose (75 mg) and magnesium stearate (15 mg). This mixture is passed through a 60-mesh sieve and packed into a No. 1 gelatin capsule.

A typical injectable preparation is produced by asceptically placing 25 mg of a water soluble salt of sterile active ingredient into a vial, then asceptically freeze-drying and sealing the vial. For use, the contents of the vial are mixed with 2 ml of physiological saline, to produce an injectable preparation.

The compounds of the invention inhibit HMG CoA reductase and, therefore, cholesterol biosynthesis. Such compounds are useful in treating:

(1) atherosclerosis (to inhibit progression of disease),
(2) hyperlipidemia (to inhibit development of atherosclerosis), and
(3) nephrotic hyperlipidemia.

In addition, the compounds of the invention increase plasma high-density lipoprotein cholesterol levels.

As HMG CoA reductase inhibitors, the compounds of the invention may also be useful in inhibiting formation of gallstones and in treating tumors. In addition, the compounds of the invention may be useful in elevating high density lipid (HDL) cholesterol levels while lowering low density lipid (LDL) cholesterol and serum triglyceride levels.

The compounds of the invention may also be employed in combination with:

(1) an antihyperlipoproteinemic agent (e.g., probucol),
(2) one or more serum cholesterol-lowering agents (e.g., "Lopid" TM, or gemfibrozil),
(3) bile acid sequestrants (e.g., cholestyramine,
(4) colestipol,
(5) DEAE-Sephadex
(6) clofibrate,
(7) nicotinic acid and its derivatives,
(8) neomycin,
(9) p-aminosalicyclic acid,
(10) lovastatin, pravastatin, visinolin (velostatin, symvastatin or sinvinolin) and the like, and
(11) one or more squalene synthetase inhibitors.

The above compounds to be employed in combination with the invention will be used in amounts indicated in the Physicians' Desk Reference (PDR).

The dose to be administered depends on the unitary dose, the symptoms, and the age and body weight of the patient. A dose for adults is preferably between 20 and 2,000 mg per day, which can be administered in a single dose or in one to four doses per day.

The compounds of this invention also have useful antifungal activities. For example, they may be used to control strains of *Penicillium sp., Aspergillus niger, Cladosporium sp., Cochliobolus miyabeorus* and *Helminthosporium cynodnotis.* For those utilities, they are first admixed with suitable formulating agents, powders, emulsifying agents or such solvents as aqueous ethanol, and then sprayed or dusted on the plants to be protected.

4. Preferred Embodiments

The following working examples represent preferred embodiments of the invention. Unless otherwise specified, all temperatures are in degrees Celsius (°C.). Compound H(1) through H(14) and I(1) through I(14) below are all within the scope of formula I.

A.
[1S-[1α(R*),3β,4β,7β,8β(2S*,4S*),8β]]-2-Methylbutanoic acid, 3-[[(1,1-dimethylethyl)dimethylsilyl]oxy]-1,2,3,7,8,8a-hexahydro-7-methyl-8-[2-(tetrahydro-4-hydroxy-6-oxo-2H-pyran-2-yl)ethyl]-1-naphthalenyl The starting material for preparation of intermediate A was [1S-[1α(R*),3β,4β,7β,8β(2S*,4S*), 8aβ]]-2-methylbutanoic acid, 3-hydroxy-1,2,3,7,8,8a-hexahydro-7-methyl-8-[2-(tetrahydro-4-hydroxy-6-oxo-2H-pyran-2-yl)ethyl]-1-naphthalenyl ester. Preparation of this starting material has been described in U.S. Pat. Nos. 3,983,140 and 4,346,227.

A solution of 8.43 g (20.7 mmol, 1.00 eq.) of the starting material in 80 ml of dry tetrahydrofuran under argon at ambient temperature was treated with 1.76 g (25.9 mmol, 1.25 eq.) of imidazole, followed by 3.44 g (22.8 mmol, 1.10 eq.) of t-butyldimethylsilyl chloride. A white precipitate formed almost immediately (5–10 sec). After stirring for 26 hours, the reaction mixture was diluted with 80 ml of ether, filtered and concentrated in vacuo. Purification of the residue by flash chromatography (with Merck silica gel; 40% ethyl acetate in hexanes) gave 7.41 g (a 69% yield) of the mono-silylated product (intermediate A) as a white solid, with a melting point of 111° to 115° C. (More typical yields for this conversion are in the range of 80 to 85%).

B.
[1S-[1α(R*),3β,4aα,7β,8β(2S*,4S*),8aβ]]-2-Methylbutanoic acid, 3-[[(1,1-dimethylethyl)-dimethylsilyl]oxy]decahydro-7-methyl-8-[2-(tetrahydro-4-hydroxy-6-oxo-2H-pyran-2-yl)-ethyl]-1-naphthalenyl ester To a degassed, argon-purged solution of 9.38 g (18.0 mmol) of intermediate A in 200 ml of ethyl acetate was added 1.4 g of 10% platinum on carbon. This suspension was subjected to 50 psi of $H_2$ in a Parr hydrogenation apparatus for 14.5 hours. Thin layer chromatography analysis indicated the complete consumption of intermediate A with generation of intermediate B and a by-product. The filtered reaction mixture was concentrated, and the products were isolated by flash chromatography. Elution with 45% hexanes in ethyl acetate gave 7.73 g (82%) of intermediate B as a clear glass.

C.
[1S-[1α(R*),3β,4aβ,7β,8β(2S*,4S*),8aβ]]-2-Methylbutanoic acid, 3-[[(1,1-dimethylethyl)-dimethylsilyl]oxy]decahydro-7-methyl-8-[2-[tetrahydro-6-oxo-4-[(phenylmethoxy)methoxy]-2H-pyran-2-yl ]-1-naphthalenyl ester The generation of benzyloxymethyl bromide was carried out by bubbling hydrobromide (HBr) through a methylene chloride ($CH_2Cl_2$) solution of benzyloxymethyl chloride for 15 minutes at 0° C., followed by stirring at ambient temperature for 45 minutes and exhaustively stripping in vacuo all volatiles.

To a solution of 23.1 g (115 mmol, 2.42 eq) of benzyloxymethyl bromide in 40 ml of methylene chloride at 0° C. was added 15.6 ml (123 mmol, 2.60 eq) of N,N-dimethylaniline and a solution of 24.9 g (47.4 mmol, 1.0 eq) of intermediate B in 50 ml of $CH_2Cl_2$. This mixture was brought immediately to ambient temperature and stirred for 18 hours. The reaction mixture was then diluted with 400 ml of ethyl acetate, washed sequentially with saturated aqueous copper sulfate ($CuSO_4$) (1×200 ml, 1×75 ml) and brine (1×150 ml), dried with magnesium sulfate ($MgSO_4$) and concentrated. The product was isolated by elution from silica gel with 10% ethyl acetate in hexanes, yielding 29.4 g (96.1%) of intermediate C as a clear, colorless, viscous oil.

D. [1S-[1α(R*),3β,4aα,7β,8β(2S*,4S*), 8aβ]]-2-Methylbutanoic acid, decahydro-3-hydroxy-7-methyl-8-[2-[tetrahydro-6-oxo-4-[(phenylmethoxy)methoxy]-2H-pyran-2-yl]ethyl]-1-naphthalenyl ester A solution of 28.8 g (44.7 mmol) of intermediate C in 400 ml of acetonitrile was cooled at −20° C. under argon and treated with three 10 ml portions of HF-pyridine over 2 hours, with warming to 0° C. after 1.5 hours. The reaction mixture was diluted with 500 ml of ethyl acetate and washed sequentially with saturated copper sulfate (aq, 2×150 ml), brine (1×250, 200 and 150 ml) and saturated sodium bicarbonate (aq, 2×250, 1×200 ml). After drying the ethyl acetate solution with sodium sulfate and concentrating, the crude product was purified by silica gel chromatography, eluting with 40% hexanes in ethyl acetate to yield 2.2 g (93.7%) of intermediate D as a clear, colorless oil.

E. [1S-[1α(R*),3β,4aα,7β,8β(2S*,4S*), 8aβ]]-2-Methylbutanoic acid, 3-(2-ethoxy-2-oxo-ethoxy)-decahydro-7-methyl-8-[2-[tetrahydro-6-oxo-4-[(phenylmethoxy)methoxy]-2H-pyran-2-yl]-ethyl]-1-naphthalenyl ester To a thoroughly degassed solution of 14.9 g (28.1 mmol, 1.00 eq) of intermediate D in 500 ml of dry methylene chloride under argon was added 30 260 mg (0.02 mol %) of [Rh(OAc)$_2$]$_2$. This mixture was stirred for 30 minutes at room temperature before initiating the slow, dropwise addition of a solution of 4.43 ml (42.1 mmol, 1.50 eq) of ethyl diazoacetate (EDA) in 20 ml of $CH_2Cl_2$ (carried out over 4 hours). Following addition of 1.1 eq of the EDA, another 60 mg of [Rh(OAc)$_2$]$_2$ was added. After complete reaction, the mixture was filtered through a pad of Celite ® with an ethereal rinse, concentrated in vacuo and chromatographed. Elution from silica gel with 30% ethyl acetate in hexanes provided 15.4 g (89.0%) of intermediate E as a clear, pale yellow oil.

F.
[1S-α(R*),3β,4aα,7β,8β(2S*,4S*),8aβ]]-2-Methylbutanoic acid, 3-(2-ethoxy-2-oxo-ethoxy)-decahydro-7-methyl-8-[2-(tetrahydro-4-hydroxy-6-oxo-2H-pyran-2-yl)ethyl]-1-naphthalenyl ester To a solution of 15.08 g (24.4 mmol) of intermediate F in 170 ml of ethyl acetate was added 2.33 g of a catalyst, 20% palladium on charcoal. This suspension was then subjected to a stream of $H_2$ for 7 hours (bubbled through reaction mixture) during which time another 2.25 g of catalyst was added in three equal portions. Following complete hydrogenolysis, the reaction mixture was filtered through a pad of Celite ®, concentrated in vacuo and chromatographed on silica gel. Elution with 40% hexanes in ethyl acetate provided 10.48 g (86.3%) of intermediate F as a clear, colorless oil.

G.
[1S-[1α(R*),3β,4aα,7β,8β(2S*,4S*),8aβ]]-2-Methyl-butanoic acid,
3-(carboxymethoxy)-decahydro-7-methyl-8-[2-(tetrahydro-4-hydroxy-6-oxo-2H-pyran-2-yl)ethyl]-1-naphthalenyl ester To a solution of 400 mg (0.81 mmol) of intermediate F in 3.0 ml of acetonitrile at 0° C. was added 1.75 ml of 1.0 N sodium hydroxide. This solution was stirred at 0° C. for 5 minutes and then at ambient temperature for 1 hour before transferring to a separatory funnel containing 20 ml of 5% potassium bisulfate (KHSO$_4$). The dihydroxy-diacid intermediate was then extracted with ethyl acetate (four times, 20 ml), dried with sodium sulfate and concentrated in vacuo. This material was then redissolved in ethyl acetate and treated with 40 μl of trifluoroacetic acid and stirred overnight at ambient temperature. The reaction mixture was concentrated and the product isolated by chromatography, eluting from silica gel with 40:1:1 dichloromethane/methanol/acetic acid to yield 316 mg (83.8%) of pure carboxylic acid-hydroxylactone as a clear, colorless oil.

H(1).
1S-1α(R*),3β,4β,7β,8β(2S*,4S*),8aβ]]-2-Methyl-butanoic acid, 3-[[(1,1-dimethyl-ethyl)dimethylsilyl]oxy]-1,2,3,7,8,8a-hexahydro-7-methyl-8-[2-(tetrahydro-4-hydroxy-6-oxo-2H-pyran-2-yl)ethyl]-1-naphthalenyl To a solution of 450 mg (0.96 mmol) of carboxylic acid, intermediate G, in 5.0 ml of dry tetrahydrofuran at 0° C. under argon was added sequentially 136 mg (1.01 mmol, 1.05 eq) of 1-hydroxybenzotriazole hydrate, 110 μl (1.01 mmol, 1.05 eq) of benzylamine, and 228 mg (1.10 mmol, 1.15 eq of 1,3-dicyclohexylcarbodiimide (DCC). The reaction mixture was brought to ambient temperature after 10 minutes and stirred for 1 hour before diluting with 20 ml of ethyl acetate, filtering through a pad of Celite ®, and concentrating in vacuo. The title compound was isolated by elution from silica gel (30% hexanes in ethyl acetate) as a colorless oil in a yield of 386 mg (72%).

Analysis calculated for $C_{32}H_{47}NO_7 \cdot (H_2O)_{1.30}$: C 67.97, H 8.53, N 2.48.
Found: C 67.94, H 8.65, N 2.51.
$[\alpha]_D = +59.4°$ (c=0.18, methylene chloride).

Utilizing the general procedure of Example H(1), intermediate G was converted into the described compounds of formula I in Examples H(2) through H(14) via reaction with the appropriate amine.

H(2).
[1S-[1α(R*),3β,4aβ,7β,8β(2S*,4S*),8aβ]]-2-Methyl-butanoic acid,
decahydro-7-methyl-3-[2-oxo-2-(phenylamino)ethoxy]-8-[2-(tetra-hydro-4-hydroxy-6-oxo-2H-pyran-2-yl)ethyl]-1-naphthalyl ester The product H(2) was isolated in a yield of 89.8%.
Analysis calculated for $C_{31}H_{45}NO_7 \cdot (H_2O)_{0.25}$: C 67.92, H 8.37, N 2.56.
Found: C 67.99, H 8.48, N 2.46.
$[\alpha]_D = +42.3°$ (c=0.17, methylene chloride).

H(3).
[1S-[1α(R*),3β,4aβ,7β,8β(2S*,4S*),8aβ]]-2-Methyl-butanoic acid,
decahydro-7-methyl-3-[2-oxo-2-[(2-phenylethyl)amino]ethoxy]-8-[2-(tetrahydro-4-hydroxy-6-oxo-2H-pyran-2--yl)ethyl]-1-naphthalenyl ester The product H(3) was isolated in a yield of 80.1%.
Analysis calculated for $C_{33}H_{49}NO_7 \cdot (H_2O)_{0.09}$: C 69.12, H 8.65, N 2.44.
Found: C 69.12, H 8.92, N 2.46. $[\alpha]_D = +29.1°$ (c=0.28, methanol).

H(4).
[1S-[1α(R*),3β,4aα,7β,8β(2S*,4S*),8aβ]]-2-Methyl-butanoic acid,
3-[2-[[(4-fluorophenyl)methyl]amino]-2-oxoethoxy]-decahydro-7-methyl-8-2-(tetrahydro-4-hydroxy-6-oxo-2H-pyran-2-yl)ethyl]-1-naphthalenyl ester The product H(4) was isolated in a yield of 83.6%.
Analysis calculated for: $C_{32}H_{46}FNO_7 \cdot (H_2O)_{1.7}$: C 63.39, H 7.21, N 2.31, F 3.13.
Found: C 63.17, H 7.82, N 2.20, F 2.91.
$[\alpha]_D = +53.6°$ (c=0.59, methanol).

H(5).
[1S-[1α(R*),3β,4aα,7β,8β(2S*,4S*),8aβ]]-2-Methyl-butanoic acid,
3-2-[bis(phenylmethyl)amino]-2-oxoethoxy]decahydro-7-methyl-8-[2-(tetrahydro-4-hydroxy-6-oxo-2H-pyran-2-yl)ethyl]-1-naphthalenyl ester The product H(5) was isolated in a yield of 84.0%.
Analysis calculated for $C_{39}H_{53}NO_7$: C 72.30, H 8.25, N 2.16.
Found: C 72.31, H 8.51, N 2.22.
$[\alpha]_D = +55.7°$ (c=0.29, methanol).

H(6).
[1S-[1α(R*),3β,4aα,7β,8β(2S*,4S*),8aβ]]-2-Methyl-butanoic acid,
decahydro-7-methyl-3-[2-[methyl(phenylmethyl)amino]-2-oxo-ethoxy-8-2-(tetrahydro-4-hydroxy-6-oxo-2H-pyran-2-yl)ethyl]-1-naphthalenyl ester The product H(6) was isolated in a yield of 85.0%.
Analysis calculated for $C_{33}H_{49}NO_7 \cdot (H_2O)_{0.30}$: C 68.67, H 8.66, N 2.43.
Found: C 68.77, H 8.78, N 2.46.
$[\alpha]_D = +58.0$ (c=0.50, methylene chloride).

H(7).
[1S-[1α(R*),3β,4aα,7β,8β(2S*,4S*),8aβ]]-2-Methyl-butanoic acid,
decahydro-7-methyl-3-[2-oxo-2-(1-pyrrolidinyl)ethoxy]-8-[2-(tetrahydro-4-hydroxy-6-oxo-2H-pyran-2-yl)ethyl]-1-naphthalenyl ester The product H(7) was isolated in a yield of 91.0%.
Analysis calculated for $C_{29}H_{47}NO_7 \cdot (H_2O)_{0.50}$: C 65.62, H 9.12, N 2.64.
Found: C 65.35, H 9.09, N 2.73.
$[\alpha]_D = +63.2°$ (c=0.29, methylene chloride).

H(8).
[1S-[1α(R*),3β,4aβ,7β,8β(2S*,4S*),8aβ]]-2-Methyl-butanoic acid,
3-[2-(butylamino)-2-oxoethoxy]decahydro-7-methyl-8-[2-(tetrahydro-4-hydroxy-6-oxo-2H-pyran-2-yl)ethyl]-1-naphthalenyl ester The product H(8) was isolated in a yield of 87.0%.

Analysis calculated for $C_{29}H_{49}NO_7\cdot(H_2O)_{0.5}$: C 65.39, H 9.46, N 2.63.

Found C 65.41, H 9.49, N 2.44.

$[\alpha]_D = +60.6°$ (c=0.50, methylene chloride).

H(9).

[1S-[1α(R*),3β,4aβ,7β,8β(2S*,4S*),8aβ]]-2-Methyl-butanoic acid,
decahydro-7-methyl-3-[2-oxo-2-(1-piperidinyl)ethoxy]-8-2-(tetrahydro-4-hydroxy-6-oxo-2H-pyran-2-yl)ethyl]-1-naphthalenyl ester The product H(9) was isolated in a yield of 83.0%.

Analysis calculated for $C_{30}H_{49}NO_7\cdot(H_2O)_{0.30}$: C 66.59, H 9.24, N 2.59.

Found: C 66.51, H 9.36, N 2.44.

$[\alpha]_D = -57.2°$ (c=0.50, methylene chloride).

H(10).

[1S-[1α(R*),3β,4aα,7β,8β(2S*,4S*),8aβ]]-2-Methyl-butanoic acid,
decahydro-7-methyl-3-[2-(4-morpholinyl)-2-oxoethoxy]-8-[2-(tetrahydro-4-hydroxy-6-oxo-2H-pyran-2-yl)ethyl]-1-naphthalenyl ester The product H(9) was isolated in a yield of 87.0%.

Analysis calculated for $C_{29}H_{47}NO_8\cdot(H_2O)_{0.30}$: C 64.13, H 8.83, N 2.58.

Found: C 64.03, H 8.86, N 2.48.

$[\alpha]_D = +58.8°$ (c=0.50, methylene chloride).

H(11).

[1S-[1α(R*),3β,4aα,7β,8β(2S*,4S*),8aβ]]-2-Methyl-butanoic acid,
decahydro-3-2-[(2hydroxyethyl)amino]-2-oxoethoxy]-7-methyl8-[2-(tetrahydro-4-hydroxy-6-oxo-2H-pyran2-yl)ethyl]-1-naphthalenyl ester The product H(11) was isolated in a yield of 87.0%.

Analysis calculated for $C_{27}H_{45}NO_8\cdot(H_2O)_{0.61}$: C 62.05, H 8.91, N 2.68

Found: C 62.15, H 8.87, N 2.58.

$[\alpha]_D = +60.0°$ (c=0.50, methylene chloride).

H(12).

[1S-[1α(R*),3β,4aβ,7β,8β(2S*,4S*),8aβ]]-2-Methyl-butanoic acid,
decahydro-3-[2-[(3-hydroxypropyl)amino]-2-oxoethoxy]-7-methyl-8-[2-(tetrahydro-4-hydroxy-6-oxo-2H-pyran-2-yl)ethyl]-1-naphthalenyl ester The product H(12) was isolated in a yield of 62.0%.

Analysis calculated for $C_{28}H_{47}NO_8$: C 63.97, H 9.01, N 2.67.

Found: C 64.22, H 9.34, N 2.29.

$[\alpha]_D = +54.2°$ (c=0.50, methylene chloride).

H(13).

[1S-[1α(R*),3β,4aβ,7β,8β(2S*,4S*),8aβ]]-2-Methyl-butanoic acid,
decahydro-3-[2-[[2-(3-methoxyphenyl)ethylamino]-2-oxo-ethoxy]-7-methyl-8[2-(tetrahydro-4-hydroxy-6-oxo-2H-pyran-2-yl)ethyl]-1-naphthalenyl ester The product H(13) was isolated in a yield of 83.0%.

Analysis calculated for $C_{34}H_{51}NO_8\cdot(_2O)_{0.20}$: C 67.46, H 8.56, N 2.31.

Found: C 67.44, H 8.75, N 2.35.

$[\alpha]_D = +54.2°$ (c=0.50, methylene chloride).

H(14).

[1S-[1α(R*),3β,4aα,7β,8β(2S*,4S*),8aβ]]-2-Methyl-butanoic acid,
decahydro-7-methyl-3-[2-oxo-2-(2-propenylamino)ethoxy]-8-[2-(tetrahydro-4-hydroxy-6-oxo-2H-pyran-2-yl)ethyl]-1-naphthalenyl ester The product H(14) was isolated in a yield of 82.0%.

Analysis calculated for $C_{28}H_{45}NO_7\cdot(H_2O)_{0.21}$: C65.75, H 8.95, N 2.74.

Found: C 65.91, H 9.15, N 2.58. $[\alpha]_D = +57.8°$ (c=0.50, methylene chloride).

I(1).

[1S-[1α(,βS*,ΔS*),2α,4aβ,6α,8β(R*),8aα]]Decahydro-β,Δ-dihydroxy-2-methyl-8-(2-methyl-1-oxobutoxy)-6-[2-oxo-2-[(phenyl-methyl)amino]ethoxy]-1-naphthaleneheptanoic acid monolithium salt To a solution of 380 mg (0.68 mmol) of hydroxylacetone H(1), prepared as described above, in 5 ml of dioxane at 0° C. was added 6.9 ml of 0.10N lithium hydroxide in dropwise fashion. This solution was brought to ambient temperature after 15 minutes and stirred for 45 minutes longer before stripping of the dioxane in vacuo. The purified product I(1) was isolated by elution from CHP-20P (water; then 15% acetonitrile in water) in a yield of 210 mg (53%) as a white, electrostatic lyophilate.

Analysis calculated for $C_{32}H_{48}NO_8Li\cdot(H_2O)_{0.81}$: C 64.45, H 8.39, N 2.35.

Found: C 64.35, H 8.22, N 2.45.

$[\alpha]_D = +39.4°$ (c=0.50, methanol).

Utilizing the general procedure of Example I(1), intermediates H(2) through H(14) were converted to the corresponding formula I compounds in examples I(2) through I(14) via saponification of the hydroxylactone.

I(2).

[1S-[1α(βS*,βS*),2a,4aβ,6α,8β(R*),8aβ]]Decahydro-β,Δ-dihydroxy-2-methyl-8-(2-methyl-1-oxobutoxy)-6-[2-oxo-2-(phenylamino)ethoxy]-1-naphthaleneheptanoic acid, monolithium salt The product I(2) was isolated in a yield of 69.9%.

Analysis calculated for $C_{31}H_{46}NO_8LI\cdot(H_2O)_{0.75}$. C 64.07, H 8.24, N 2.41.

Found: C 64.14, H 8.43, N 2.34.

$[\alpha]_D = +35.2°$ (c=0.50, methanol).

I(3).

[1S-[1α(βS*,ΔS*),2α,4aβ,6α,8β(R*),8aα]]-Decahydro-β,Δ-dihydroxy-2-methyl-8-(2-methyl-1-oxobutoxy)-6-[2-oxo-2-[(2-phenylethyl)amino]ethoxy]-1-naphthaleneheptanoic acid, monolithium salt The product I(3) was isolated in a yield of 65.5%.

Analysis calculated for $C_{33}H_{50}NO_8LI\cdot(H_2O)_{0.66}$: C 65.22, H 8.51, N 2.31.

Found: C 65.25, H 8.58, N 2.28.

$[\alpha]_D = +42.6°$ (c=0.50, methanol).

I(4).

[1S-[1α(βS*,ΔS*),2α,4aβ,6α,8β(R*),8aα]]-6-[2-[[(4-Fluorophenyl)methyl]amino]-2-oxoethoxy]decahydro-β,Δ-dihydroxy-2-methyl-8-(2-methyl-1-oxobutoxy)-1-naphthaleneheptanoic acid, monolithium salt The product I(4) was isolated in a yield of 79.7%.

Analysis calculated for $C_{32}H_{47}FNO_8LI\cdot(H_2O)_{0.75}$: C 62.68, H 7.97, N 2.29.

Found: C 62.79, H 7.83, N 2.25.

$[\alpha]_D = +44.6°$ (c=0.50, methanol).

I(5).
[1S-[1α(βS*,ΔS*),2α,4aβ,6α,8α(R*),8aα]]-6-[2-[B-is(phenylmethyl)amino]-2-oxoethoxy]-decahydro-β,Δ-dihydroxy-2-methyl-8-(2-methyl-1-oxobutoxy)-1-naphthaleneheptanoic acid, monolithium salt The product I(5) was isolated in a yield of 59.6%.
Analysis calculated for $C_{H54}NO_8Li\cdot(H_2O)_{0.75}$: C 6B.36, H 8.16, N 2.04.
Found: C 68.23, H 8.14, N 1.95.
$[\alpha]_D = +36.4°$ (c=0.50, methanol).

I(6).
[1S-[1α(βS*,ΔS*),2α,4aβ,6α,8β(R*),8aα]]-Decahydro-β,Δ-dihydroxy-2-methyl-8-(2-methyl-1-oxobutoxy)-6-[2-[methyl(phenylmethyl)amino]-2-oxoethoxy]-1-naphthaleneheptanoic acid, monolithium salt The product I(6) was isolated in a yield of 83.0%.
Analysis calculated for $C_{33}H_{50}NO_8Li\cdot(H_2O)_{0.43}$: C 65.68, H 8.49, N 2.32.
Found: C 65.68, H 8.58, N 2.13.
$[\alpha]_D = +38.4°$ (c=0.50, methylene chloride).

I(7).
[1S-]1α(βS*,ΔS*),2α,4aβ,6α,8β(R*),8aα]]-Decahydro-β,Δ-dihydroxy-2-methyl-8-(2-methyl-1-oxobutoxy)-6-[2-oxo-2-(1-pyrrolidinyl)ethyoxy]-1-naphthaleneheptanoic acid, monolithium salt The product I(7) was isolated in a yield of 81.0%.
Analysis calculated for $C_{29}H_{48}NO_8Li\cdot(H_2O)_{0.75}$. C 62.28, H 8.92, N 2.51.
Found: C 62.27; H 8.95, N 2.47.
$[\alpha]_D = +41.0$ (c=0.50, methylene chloride).

I(8).
[1S-[1α(βS*,ΔS*),2α,4aβ,6α,8β(R*),8aα]]-3-[2-(Butylamino)-2-oxoethoxy]decahydro-β,Δ-dihydroxy-2-methyl-8-(2-methyl-1-oxobutoxy)-1-naphthaleneheptanoic acid, monolithium salt The product I(8) was isolated in a yield of 82.0%.
Analysis calculated for $C_{29}H_{50}NO_8LI\cdot(H_2O)_{1.06}$: C 61.45, H 9.27, N 2.47.
Found: C 61.53, H 9.22, N 2.39.
$[\alpha]_D = +37.2°$ (c=0.50, methylene chloride).

I(9).
[1S-[1α(βS*,ΔS*),2α,4aβ,6α,8β(R*),8aα]]-Decahydro-β,Δ-dihydroxy-2-methyl-8-(2-methyl-1-oxobutoxy)-6-[2-oxo-2-(1-piperidinyl)ethoxy]-1-naphthaleneheptanoic acid, monolithium salt The product I(9) was isolated in a yield of 59.0%.
Analysis calculated for $C_{30}H_{50}NO_8Li\cdot(H_2O)_{0.50}$: C 63.36, H 9.04, N 2.46.
Found: C 63.32, H 9.19, N 2.41.
$[\alpha]_D = +41.2°$ (c=0.50, methanol).

I(10).
[1S-[1α(βS*,ΔS*),2α,4aβ,6α,8β(R*),8aα]]-Decahydro-β,Δ-dihydroxy-2-methyl-8-(2-methyl-1-oxobutoxy)-6-[2-(4-morpholinyl)-2-oxoethoxy]-1-naphthaleneheptanoic acid, monolithium salt The product I(10) was isolated in a yield of 65.0%.
Analysis calculated for $C_{29}H_{48}NO_9Li\cdot(H_2O)_{0.50}$: C 61.04, H 8.65, N 2.46.
Found: C 61.14, H 8.92, N 2.36.
$[\alpha]_D = +41.8°$ (c=0.50, methanol).

I(11).
[1S-1α(βS*,ΔS*),2α,4aβ,6α,8β(R*),8aα]]-Decahydro-β,A-dihydroxy-6-[2-[(2-hydroxyethyl)amino]-2-oxoethoxy]-2-methyl-8-(2-methyl-1-oxobutoxy)-1-naphthaleneheptanoic acid, monolithium salt The product I(11) was isolated in a yield of 67.0%.
Analysis calculated for $C_{27}H_{46}NO_9(H_2O)_{1.57}$: C 57.51, H 8,78, N 2.48.
Found: C 57.47, H 8.71, N 2.52.
$[\alpha]_D = +44.2°$ (c=0.50, methanol.

I(12).
[1S-[1α(βS*,ΔS*),2α,4aβ,6α,8β(R*),8aα]]-Decahydro-β, Δ-dihydroxy-6-[2-(3-hydroxypropyl)amino]-2-oxoethoxy]-2-methyl-8-(2-methyl-1-oxobutoxy)-1-naphthaleneheptanoic acid, monolithium salt The product I(12) was isolated in a yield of 90.0%.
Analysis calculated for $C_{29}H_{48}NO_9Li\cdot(H_2O)_{0.50}$: C 60.21, H 8.84, N 2.51.
Found: C 60.15, H 8.81, N 2.49.
$[\alpha]_D = +42.2°$ (c=0.50, methanol).

I(13).
[1S-[1α(βS*,ΔS*),2α,4aβ,6α,8β(R*),8aα]]-Decahydro-β,Δ-dihydroxy-3-[2-[[2-(3-methoxyphenyl)ethyl]amino]-2-oxoethoxy]-7-methyl-8-(2-methyl-1-oxobutoxy)-1-naphthaleneheptanoic acid, monolithium salt The product I(13) was isolated in a yield of 60.0%.
Analysis calculated for $C_{34}H_{52}NO_9NO_9Li$: C 65.26, H 8.38, N 2.24.
Found: C 64.79, H 8.53, N 2.47.
$[\alpha]_D = +39.0°$ (c=0.50, methanol).

I(14). [1S-[1α(βS*,ΔS*),2α,4aβ,6α,8β(R*),8aα]]-Decahydro-β,Δ-dihydroxy-2-methyl-8-(2-methyl-1-oxobutoxy)-6-[2-oxo-2-(2-propenylamino)ethoxy]-1-naphthaleneheptanoic acid, monolithium salt The product I(14) was isolated in a yield of 65.0%.
Analysis calculated for $C_{28}H_{46}NO_8Li\cdot(H_2O)_{0.30}$: C 62.63, H 8.75, N 2.61.
Found: C 62.58, H 8.99, N 2.71.
$[\alpha]_D = +44.0°$ (c=0.50, methanol).

The foregoing represent preferred embodiments of this invention. Other embodiments are possible, as will be apparent to those skilled in the art. The foregoing examples are illustrative rather than limiting; the scope of this invention is limited only by the claims appended hereto.

What is claimed is:
1. A compound of the formula

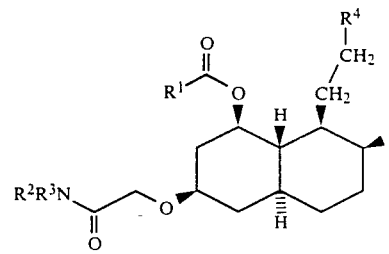

wherein:
$R^1$, $R^2$ and $R^3$ are independently selected from:
(1) alkyl, (2) substituted alkyl in which one or more substituents are selected from
  (a) halogen,
  (b) hydroxyl,
  (c) alkoxy,
  (d) alkoxycarbonyl,
  (e) acyloxy,
  (f) cycloalkyl,
  (g) phenyl,
  (h) substituted phenyl in which one or more substituents are X or Y,
  (i) alkyl-$S(O)_n$,
  (j) cycloalkyl-$S(O)_n$,
  (k) phenyl-$S(O)_n$,
  (l) substituted phenyl-$S(O)_n$ in which one or more substituents are X or Y, and
  (m) oxo,
(3) alkoxy,
(4) alkenyl,
(5) cycloalkyl,
(6) substituted cycloalkyl in which one or more substitutents are selected from
  (a) alkyl,
  (b) substituted alkyl in which one or more substituents are selected from
    (i) halogen,
    (ii) hydroxy,
    (iii) alkoxy,
    (iv) alkoxycarbonyl
    (v) acyloxy
    (vi) phenyl
    (vii) substituted phenyl in which one or more substituents are X and Y,
    (viii) alkyl-$S(O)_n$,
    (ix) cycloalkyl-$S(O)_n$,
    (x) phenyl-$S(O)_n$,
    (xi) substituted phenyl-$S(O)_n$ in which one or more substitutents are X and Y, and
    (xii) oxo,
  (c) alkyl-$S(O)_n$,
  (d) cycloalkyl-$S(O)_n$,
  (e) phenyl-$S(O)_n$,
  (f) substituted phenyl-$S(O)_n$ in which one or more substituents are X or Y,
  (g) halogen,
  (h) hydroxy,
  (i) alkoxy,
  (j) alkoxycarbonyl,
  (k) acyloxy,
  (l) phenyl, and
  (m) substituted phenyl in which one or more substituents are X or Y,
(7) phenyl,
(8) substituted phenyl in which one or more substituents are X or Y,
(9) amino,
(10) alkylamino,
(11) dialkylamino,
(12) phenylamino,
(13) substituted phenylamino in which one or more substituents are X or Y,
(14) alkyl(substituted phenyl)amino in which one or more substituents are X or Y,
(15) phenylalkylamino,
(16) di(phenylalkyl)amino,
(17) substituted phenylalkylamino in which one or more substituents are X or Y,
(18) a member selected from
  (a) piperidinyl,
  (b) pyrrolidinyl,
  (c) piperazinyl,
  (d) morpholinyl,
  (e) thiomorpholino,
  (f) histaminyl,
  (g) 3-aminomethylpyridinyl, and
(19) hydroxy substituted alkylamino,
X and Y are independently hydrogen, halogen, trifluoromethyl, alkyl, nitro, alkoxy, or cyano;
n is 0, 1, or 2;

$R^4$ is 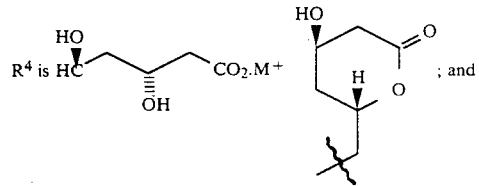

$M+$ is hydrogen, ammonium, or an alkali metal; and wherein:
"alkyl" and "alkoxy" refer to straight and branched chain groups of 1 to 8 carbon atoms;
"alkenyl" refers to straight and branched chain groups having 2 to 10 carbon atoms;
"cycloalkyl" refers to cyclic saturated hydrocarbon groups having 3 to 12 carbon atoms and to such groups substituted with 1 to 2 halogens, 1 or 2 alkyl groups, and/or 1 or 2 alkoxy groups.

2. The compound of claim 1, wherein $R^2$ is alkoxycarbonyl of one to five carbon atoms.

3. The compound of claim 1, wherein $R^2$ is phenyl.

4. The compound of claim 1, wherein $R^3$ is alkyl having one to ten carbon atoms.

5. The compound of claim 1, wherein $R^4$ is

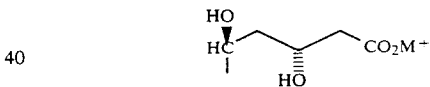

and $M+$ is lithium.

6. The compound according to claim 1, 1S-[1α(R*),3β,4aα,7β,8β(2S*,4S*),8aβ]]-2-methyl-butanoic acid, decahydro-7-methyl-3-[2-oxo-2-[(phenylmethyl)amino]ethoxy]-8-[2-(tetrahydro-4-hydroxy-6-oxo-2H-pyran-2-yl)ethyl]-1-naphthalenyl ester.

7. The compound according to claim 1, 1S-[1α(,bS*,-dS*),2α,4aβ,6α,8β(R*),8aα]]-decahydro-βΔ-dihydroxy-2-methyl-8-(2-methyl-1-oxobutoxy)-6-[2-oxo-2-[(phenylmethyl)amino]ethoxy]-1-naphthaleneheptanoic acid, monolithium salt.

8. A method of treating atherosclerosis, which comprises administering an effective dose of a compound as described in claim 1.

9. A method of treating hyperlipidemia, which comprises administering an effective dose of a compound as described in claim 1.

10. A method of treating nephrotic hyperlipidemia which comprises administering an effective dose of a compound as described in claim 1.

11. A method of controlling strains of fungus on a plant, which comprises treating the plant with an effective amount of a compound as described in claim 1.

12. A method of increasing plasma high-density lipoprotein cholesterol levels, which comprises administering an effective dose of a compound as described in claim 1.
13. A compound of the formula
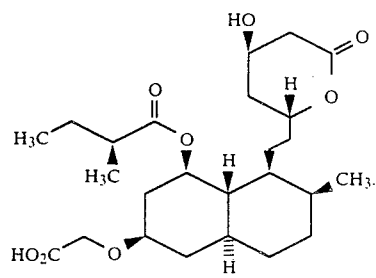
* * * * *